(12) United States Patent
Huang et al.

(10) Patent No.: US 6,509,104 B2
(45) Date of Patent: *Jan. 21, 2003

(54) ANTITHROMBOGENIC POLYMER COATING

(75) Inventors: Zhi Heng Huang, San Ramon, CA (US); William F. McDonald, Utica, OH (US); Stacy C. Wright, Flint, MI (US); Andrew C. Taylor, Ann Arbor, MI (US)

(73) Assignee: Michigan Biotechnology Institute, Lansing, MI (US)

( * ) Notice: Subject to any disclaimer, the term of this patent is extended or adjusted under 35 U.S.C. 154(b) by 37 days.

This patent is subject to a terminal disclaimer.

(21) Appl. No.: 09/730,098

(22) Filed: Dec. 5, 2000

(65) Prior Publication Data

US 2002/0068183 A1 Jun. 6, 2002

(51) Int. Cl.[7] .................. B32B 27/08; B32B 27/34; B05D 3/00; B05D 1/00

(52) U.S. Cl. ................ 428/474.4; 428/411.1; 428/423.5; 427/2.1; 427/322; 427/331; 128/DIG. 22; 523/112; 525/50; 525/54.1; 525/54.2; 525/54.22

(58) Field of Search ................... 528/312, 313, 528/310, 315, 318, 316, 322, 335; 427/3.1, 322, 331; 128/DIG. 22; 525/50, 54.1, 54.2, 54.22; 428/411.1, 423.5, 474.4; 523/112

(56) References Cited

U.S. PATENT DOCUMENTS

| | | | |
|---|---|---|---|
| 4,217,338 A | 8/1980 | Quash ........................... 424/1 |
| 4,302,368 A | * 11/1981 | Dudley et al. ............... 523/112 |
| 4,326,532 A | 4/1982 | Hammar ...................... 128/349 |
| 4,419,444 A | 12/1983 | Quash ........................... 435/7 |
| 4,720,512 A | * 1/1988 | Hu et al. ..................... 523/112 |
| 4,786,556 A | * 11/1988 | Hu et al. ..................... 428/412 |
| 4,810,784 A | 3/1989 | Larm .......................... 536/20 |
| 4,865,870 A | 9/1989 | Hu et al. ....................... 427/2 |
| 4,874,813 A | 10/1989 | O'Shannessy ............. 525/54.1 |
| 4,948,836 A | 8/1990 | Solomon et al. ........... 525/54.1 |
| 4,987,181 A | * 1/1991 | Bichon et al. .............. 525/54.1 |
| 5,104,931 A | 4/1992 | Fleminger et al. .......... 525/54.1 |
| 5,316,912 A | 5/1994 | Heimgartner et al. ........ 435/7.9 |
| 6,087,462 A | * 7/2000 | Bowers et al. .............. 526/277 |
| 6,121,027 A | 9/2000 | Clapper et al. ................ 514/2 |
| 6,153,724 A | 11/2000 | Hollingsworth ............. 528/310 |
| 6,319,674 B1 | * 11/2001 | Fulcrand et al. ............. 435/7.1 |

FOREIGN PATENT DOCUMENTS

| | | |
|---|---|---|
| JP | 59015401 | 1/1984 |
| WO | WO 95/05400 A1 | 2/1995 |
| WO | WO 00/17254 | 3/2000 |

OTHER PUBLICATIONS

Larrson et al., The Search for Thromboresistance Using Immobolized Heparin, Ann. NY Acad. Sci. 516, 102–115, 1987. The month in the date of publication is not available.

Hoffman et al., A New Method for Covalent Coupling of Heparin and other Glycosaminoglycans to Substances Containing Primary Amino Groups, Carbohydr. Res. 117, 328–331, 1983. The month in the date of publication is not available.

O'Shannessy et al., Immobilization of Glycoconjugates by Their Oligosaccharides: Use of Hydrazido–Derivatized Matrices, Anal. Biochem., 191, 1–8, 1990. The month in the date of publication is not available.

Ito et al., Preparation of High Capacity Affinity Adsorbents Using New Hydrazino–Carriers and Their Use for Low and High Performance Affinity Cheomatography of Lectins, J. Biochem. (Tokyo), 99, 1267–1272. The date of publication is not available.

Junowicz et al., The Derivatization of Oxidized Polysaccharides for Protein Immobilization and Affinity Chromatography Biochim. Biophys. Acta 428, 157–165, 1976.

Micron et al., Polyacrylhyrdazio–Agarose: Preparation via Periodate Oxidation and use for Enzyme Immobilization and Affinity Chromatography, J. Chromatogr., 215, 55–63, 1981.

Heimgartner, et al., Polyacrylic Polyhydrazides as Reagents for Detection of Glycoproteins, Anal. Biochem., 181, 182–189, 1989.

Fleminger et al., Oriented Immobilization of Peridate–Oxidized Monoclonal Antibodies on Amino and Hydrazide Derivatives of Eupergit C, Applied Biochem., 23, 123–137, 1990.

Kitagaki et al., Dermatan Sulfate–Reactive Lectin from Chicken Liver, J. Biochem. 98, 385–393, 1985.

Del Rosso et al., Binding of the Basement–Membrane Glycoprotein Lamnin to Glycosaminoglycans, Biochem. J., 199, 699–704, 1981.

(List continued on next page.)

Primary Examiner—P. Hampton-Hightower
(74) Attorney, Agent, or Firm—Quarles & Brady LLP

(57) ABSTRACT

An article having a non-thrombogenic surface and a process for making the article are disclosed. The article is formed by (i) coating a polymeric substrate with a crosslinked chemical combination of a polymer having at least two amino substituted side chains, a crosslinking agent containing at least two crosslinking functional groups which react with amino groups on the polymer, and a linking agent containing a first functional group which reacts with a third functional group of the crosslinking agent, and (ii) contacting the coating on the substrate with an antithrombogenic agent which covalently bonds to a second functional group of the linking agent. In one example embodiment, the polymer is a polyamide having amino substituted alkyl chains on one side of the polyamide backbone, the crosslinking agent is a phosphine having the general formula $(A)_3P$ wherein A is hydroxyalkyl, the linking agent is a polyhydrazide and the antithrombogenic agent is heparin.

55 Claims, 4 Drawing Sheets

OTHER PUBLICATIONS

Satoh et al., Immobilization of Saccharides and Peptides on 96–Well Microtiter Plates Coated with Methyl Vinyl ether–Maleic Anhydride Copolymer, *Anal. Biochem.*, 260, 96–102, 1998.

Isosaki et al., Immobilization of Protein Ligands with Methyl Vinyl Ether–Maleic Anhydride Copolymer, *J. Chromatogr.*, 597, 123–128,1992.

Henderson et al., Immobilised Phosphines Incorporation the Chiral Bioploymers Chitosan and Chitin, *J. Chem. Soc., Chem. Commun.*, 9, 1863–1864, 1994.

Petach et al., A New Coupling Reagnet for the Covalent Immobilisation of Enzymes, *J. Chem. Soc., Chem. Commun.*, 17, 2181–2182, 1994.

Cochrane et al., Application of Tris(hydroxymethyl) Phophine as a Coupling Agent for Alcohol Dehydrogenase Immobilization, *Enzyme Microbial Technol.*, 18, 373–378, 1996.

Oswald et al., Properties of a Thermostable B–Glucosidase Immobilized Using Tris(hydroxmethyl) Phosphine as a Highly Effective Coupling Agent, *Enzyme Microbial Technol.*, 23, 14–19, 1998.

Vercruysse et al., Synthesis and in Vitro Degradation of New Polyvalent Hydrazide Cross–Linked Hydrogels of Hyaluronic Acid, *Bioconj. Chem.*, 8, 686–694, 1997.

Prestwich et al., Controlled Chemical Modification of Hyaluronic Acid: Synthesis, Applications, and Biodegredation of Hydrazide Derivatives, *J. Controlled Release*, 53, 93–103, 1998.

Inman et al., Synthesis of Large Haptenic Compounds Having a Covalent Functional Group That Permits Convalent Linkage to Proteins, Cell Surfaces, *Immunochemistry,* 10, 153–163, 1973.

Ellis et al., Water–Soluble Tris(hydroxymethyl) Phospine Complexes with Nickel, Palladium, and Platinum, *Inorg. Chem.*, 31, 3026–3033, 1992.

Smith et al., Colormetric Method for the assay of Heparin Content in Immobilized Heparin Preparations, *Anal. Biochem.*, 109:466–473, 1980.

Dick et al., A New Method for Direct Detection of Heparin in Surface–Modified Intraocular Lense, *Ophthalmologica,* 211, 75–78, 1997.

Jaques, L.B., Determination of Heparin and Related Sulfated Mucopolysaccharides, Methods of Biochem. Anal., V.24 (D. Glick, ed.), pp. 205–243, Wiley & Sons, NY, 1977.

Lin et al., Preparation of Surface–modified Albumin Nanospheres, Biomaterials, V. 18, N. 7, 559–565, 1997.

Marconi et al., New Polyurethane Compsitions able to bond high Amounts of both Albumin and Heparin, V. 16, N. 6, 449–456, 1995.

Tsai et al., Biocompatible Coatings with High Albumin Affinity, ASAIO Transactions, 307–310, 1990.

PCT International Search Report for PCT/US01/44597.

\* cited by examiner

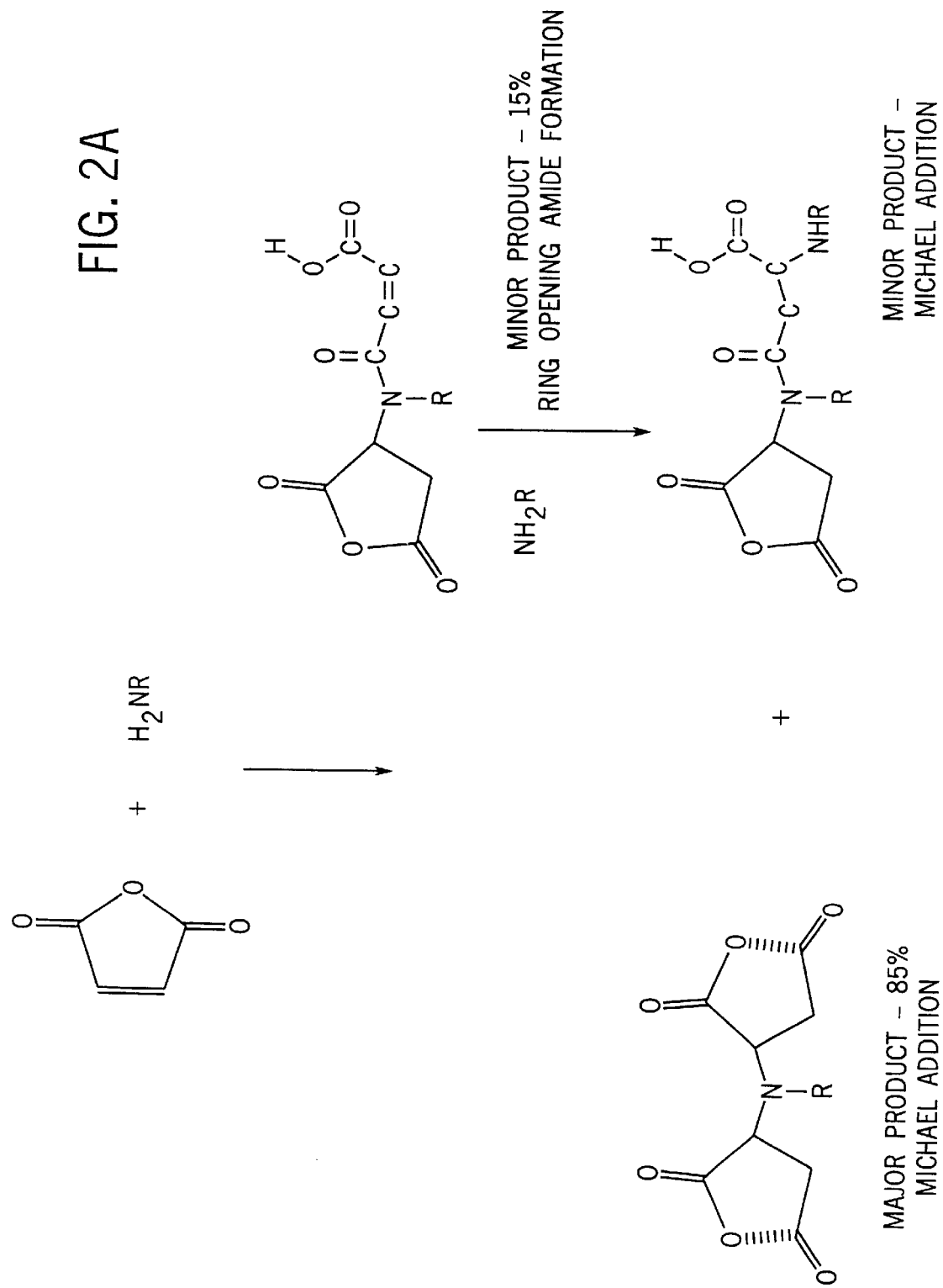

ANTITHROMBOGENIC POLYMER COATING

BACKGROUND OF THE INVENTION

1. Field of the Invention

This invention relates to an article having a non-thrombogenic surface and a process for making the article. More particularly, this invention relates to an article formed by (i) coating a polymeric substrate with a crosslinked chemical combination of a polymer having at least two amino substituted side chains, a crosslinking agent containing at least two crosslinking functional groups which react with amino groups on the polymer, and a linking agent containing a first functional group which reacts with a third functional group of the crosslinking agent, and (ii) contacting the coating on the substrate with an antithrombogenic agent, such as heparin, which covalently bonds to a second functional group of the linking agent.

2. Description of the Related Art

It is well known that when blood comes into contact with a surface other than the natural wall of a blood vessel, the activation of certain circulating substances results in the coagulation of the blood. If thrombi are formed on portions of the surface which contact blood flow, there is a risk that the thrombi will be released and cause serious blood circulation disturbances called thrombosis. As a result, extensive investigations have been undertaken over many years to find materials having a reduced tendency to form thrombosis. This area of research has become increasingly important with the development of various objects and articles which can be in contact with blood, such as artificial organs, vascular grafts, probes, cannulas, catheters and the like.

Synthetic polymeric materials have come to the fore as preferred materials for such articles. However, these polymeric materials have the major drawback of being thrombogenic. Accordingly, numerous procedures for rendering a polymeric surface non-thrombogenic have been proposed. (As used herein, "non-thrombogenic" and "antithrombogenic" refer to any material which inhibits thrombus formation on a surface.) One well known approach for counteracting thrombogenicity of a polymeric surface has been the use of antithrombogenic agents or anticoagulants such as heparin. Heparin is a highly sulfated dextrorotatory mucopolysaccharide composed of D-glucosamine and D-glucuronic acid residues, and is known to prolong the clotting time of blood.

Various general methods for the attachment of heparin to otherwise thrombogenic polymeric surfaces are known. In one general method, heparin is ionically bound to a surface. Heparin is an anionic compound which easily forms ion complexes with cationic compounds. As a result, it has been proposed to attach a cationic substance to a surface and thereafter ionically bind heparin to the cationic substance. For example, U.S. Pat. No. 3,617,344 discloses a method in which a polymeric surface is chemically modified to include a chloromethyl group, the chloromethyl group is aminated to provide a quaternary ammonium halide, and the halide is reacted with sodium heparin to ionically bond heparin to the surface. One disadvantage with ionically bound systems is that the heparin can leach off the surface when contacted with blood or other fluids.

Because of the leachability of ionically bound heparin, another general method for the attachment of heparin to otherwise thrombogenic polymeric surfaces has been developed wherein heparin is covalently bound to a surface. Immobilization of heparin to artificial blood-contacting materials through covalent bonding has proven to be a successful approach for achieving a non-thrombogenic surface suitable for use in medical applications. Previous efforts to covalently immobilize heparin include: (1) the formation of an amide linkage derived from the —$CO_2H$ of heparin and a polymer carrying an —$NH_2$-side-chain by coupling with a water-soluble carbodiimide (see, for example, U.S. Pat. No. 4,521,564); (2) the formation of an ether group by reaction of the —OH group of the sugar ring with an epoxidized support; and (3) the linking of heparin at its reducing end to an —$NH_2$ containing solid matrix by reductive amination (see U.S. Pat. No. 4,810,784). According to the last approach, a polyethylene substrate was modified by (i) brief treatment with $KMnO_4$ in concentrated sulfuric acid to generate anionic (—$CO_2H$/$SO_3H$) sites, (ii) incubation with 0.01%. polyethylenimine, and (iii) coupling of the resulting $NH_2$-rich surface with heparin by reductive amination ($NaBH_3CN$ in buffer at pH 3.5). Apart from the advantage of its long-term stability (reportedly up to several months), the heparin incorporated this way (the so-called "end-point attachment") mimics its natural configuration, allowing maximal retention of its antithrombogenic properties.

It has been established further, that the end-point attachment technique can be successfully extended to polymeric carriers bearing surface hydrazide groups (See D. J. O'Shannessy and M. Milcheck, Anal. Biochem. 191, 1–8, 1990). Hydrazide is much more active over —$NH_2$ as a nucleophile in reaction with aldehydes (including all reducing sugars), while possessing lower basicity in comparison to amines (pK for hydrazides: ~3, for primary amines: ~7). Notable advantages of using a hydrazide matrix for immobilization of reducing sugars, including heparin, are: (1) a faster reaction (about 30-fold for simple saccharides) than using the —$NH_2$ supports (See Y. Ito, Y. Yamasaki, N. Seno, and I. Matsumoto, J. Biochem. Tokyo, 99, 1267–1272, 1986); (2) the reaction of hydrazide with —CHO is an irreversible process and therefore, the need for further stabilization by $NaBH_3CN$ reduction can be partly avoided or totally eliminated; and (3) unlike primary amines, hydrazides remain unprotonated at slightly acidic pH levels (as low as 3–4.7). Reaction under these conditions will help to minimize the possible by-products originating from the —$NH_2$ groups in the substrate and coating materials.

A number of solid supports (mostly in the form of polysaccharide beads) containing hydrazide groups are presently commercially available for use as adsorbents in affinity chromatography. These hydrazide supports may be prepared by: (1) diimide coupling of polymeric amines with p-hydrazinobenzoic acid; (2) direct condensation of an epoxy-containing polymer with a dihydrazide like adipic dihydrazide; and (3) coupling of polymeric active esters with hydrazine. The preparation of hydrazide supports and their application in affinity chromatography of oligosaccharides, polysaccharides, glycoproteins, and enzymes carrying sugar units is described in a number of patents (See, for example, U.S. Pat. Nos. 4,217,338, 4,419,444, 4,874,813, 4,948,836, 5,104,931, 5,316,912, and Japanese Patent Publication No. 59015401.) Immobilization is carried out by reaction of the hydrazide reagent with the reducing terminus of the target molecule. Alternatively, the hydrazide coupling is preceded by a periodate-oxidation (to split the vicinal diols of sugar unit and provide newly generated —CHO groups) and finally completed by $NaBH_3CN$ reduction.

The preparation of hydrazide matrices has been reported in the technical literature. For example, (1) the preparation of modified polysaccharide matrices (cellulose, Sephadex, and Sepharose) through $NaIO_4$-oxidation and subsequent reaction with adipic dihydrazide is described by E. Junowicz, and S. E. Charm at *Biochim. Biophys. Acta* 428, 157–165, 1976; (2) the preparation of polyacrylhydrazide-agarose by periodate oxidation of agarose followed by reaction with polyacrylhydrazide is described by T. Miron and M. Wilchek at *J. Chromatogr.* 215, 55–63, 1981; (3) the preparation of polyacrylamide-polyhydrazides from the corresponding N-hydroxysuccinimide-ester and hydrazine and use in the analysis of glycoproteins is described by U. Heimgartner, B. Kozulic, and K. Mosbach at *Anal Biochem.* 181, 182–189, 1989; and (4) the preparation of hydrazide-derivatized Eupergit C beads from Eupergit C [a poly (methyl methacrylamide) bearing epoxide group] and adipic dihydrazide is described by G. Fleminger, E. Hadas, T. Wolf, and B. Solomon at *Applied Biochem. Biotechnol.* 23, 123–137, 1990.

Other techniques for the immobilization of heparin and related sulfated sugars on various substrates are described in the technical literature. For example, (1) heparin and dermatin sulfate immobilized on hydrazide-Toyopearl for isolation of lectin is described by H. Hitagaki, H. Motsumoto, H. Sasaki, and N. Seno at *J. Biochem. (Tokyo)*, 98, 385–393, 1985; (2) partially periodate-oxidized heparin and others on immobilized adipic dihydrazide-agarose for studying glycoprotein-heparin interactions is described by M. Del Rosso et al. at *Biochem. J.* 199, 699–704, 1981; and (3) heparin immobilized on adipic dihydrazide modified poly (methyl vinyl ether-alt-maleic anhydride) is described by A. Satoh, K. Kojima, T. Koyama, H. Ogawa, and I. Matsumoto, at *Anal. Biochem.* 260, 96–102, 1998 and by K. Isosaki, N. Seno, I. Matsumoto, T. Koyama, and S. Moriguchi, at *J. Chromatogr.* 597, 123–128, 1992 for use in ELISA.

Even though various techniques are known for attaching heparin and other antithrombogenic agents to a substrate, there is still a need for an improved antithrombogenic polymer coating that may be easily applied to a substrate to provide a material which has excellent biological and chemical stability towards blood and which retains its antithrombogenic properties in a permanent and non-leachable fashion when in contact with blood for prolonged periods.

SUMMARY OF THE INVENTION

The foregoing needs are met by an article having a non-thrombogenic surface according to the present invention and by a process for rendering the surface of a substrate non-thrombogenic according to the present invention. An article according to the invention comprises a substrate, a coating disposed on at least a portion of the substrate, and an antithrombogenic agent covalently bonded to the coating. The coating comprises a crosslinked chemical combination of (i) a polymer having side chains along a backbone forming the polymer, at least two of the side chains containing an amino group, (ii) a crosslinking agent containing at least two functional groups capable of reacting with the amino groups, and (iii) a linking agent containing a first functional group and a second functional group, the first functional group capable of reacting with the crosslinking agent's functional groups. The antithrombogenic agent is covalently bonded to the second functional group of the linking agent.

The substrate of an article according to the invention may comprise any polymeric material conventionally used to fabricate articles commonly used in contact with blood. The substrate serves as a support for the coating and the antithrombogenic agent.

The polymer used in the coating comprises a polymer having side chains along a backbone forming the polymer wherein at least two of the side chains contain an amino group (—NRH, —$NH_2$, —$NRH_2^+$, —$NH_3^+$). In one example embodiment, the polymer is a polyamide having amino substituted alkyl chains on one side of the polymer backbone.

The crosslinking agent used in the coating contains at least two functional groups capable of reacting with the amino groups of the polymer used in the coating. In one example of the crosslinking agent used in the coating, the crosslinking agent is selected from the group consisting of phosphines having the general formula $(A)_3P$, wherein A is hydroxyalkyl. One more specific example of the crosslinking agent used in the coating is tris(hydroxymethyl) phosphine.

The linking agent used in the coating contains a first functional group and a second functional group wherein the first functional group is capable of reacting with a third functional group of the crosslinking agent. In one example of the linking agent used in the coating, the linking agent is a polyhydrazide, that is, the linking agent includes at least two functional groups having the formula —$CONHNH_2$. One specific example of the linking agent used in the coating is adipic dihydrazide.

The antithrombogenic agent used in an article according to the invention may be any material which inhibits thrombus formation on its surface, such as by reducing platelet aggregation, dissolving fibrin, enhancing passivating protein deposition, or inhibiting one or more steps within the coagulation cascade. In one example of the antithrombogenic agent, the antithrombogenic agent is selected from heparin, prostaglandins, urokinase, streptokinase, sulfated polysaccharide, albumin and mixtures thereof. One more specific example of the antithrombogenic agent is heparin.

The article having a non-thrombogenic surface may be produced by a process according to the invention in which a polymer having at least two amino substituted side chains is mixed with a crosslinking agent and a linking agent to produce a polymer solution. The crosslinking agent contains at least two crosslinking functional groups which react and combine with amino groups on the polymer, and a third functional group. The linking agent contains a first functional group which reacts and combines with the third functional group of the crosslinking agent, and a second functional group. The polymer solution is coated on at least a portion of a substrate to produce a crosslinked polymer coating on the substrate. At least a portion of the crosslinked polymer coating on the substrate is then contacted with an antithrombogenic agent such that the antithrombogenic agent covalently bonds to the second functional group of the linking agent.

In an example embodiment of the invention, the versatile chemical methodology of the invention allows the attachment of heparin through covalent linkage to a two-dimensional polymer carrier that is deposited on a polymeric substrate (e.g., polydimethylsiloxane, polyurethane, and polypropylene). The two-dimensional polymers have a backbone of repeating β-amino acid units with long aliphatic side-chain and free NH— and $NH_2$— substituents and are synthesized by condensation of 2(5H)-furanone, or maleic acid derivatives (such as anhydride, esters, and so on) with a long-chain amine (e.g., tetradecylamine) and a polyamine (e.g., pentaethylenehexamine). Coupling of the two-dimensional polymer with tris(hydroxymethyl)phosphine (the crosslinking agent) and adipic dihydrazide (or other di-, tri-, and polyhydrazide linking agents having at least two —CONHNH$_2$ groups) results in the formation of a triblock polymer with pendant hydrazide groups. The coupling solution is used (without isolation) directly for the preparation of an intermediary reactive coating. The latter is then allowed to react with heparin or heparin/sodium cyanoborohydride in aqueous medium to produce a covalently bonded antithrombogenic surface with remarkably enhanced heparin content (greater than or equal to 10 micrograms/cm$^2$) and improved operational stability. Direct heparinization with sodium heparin forms a hydrazone, while heparinization by reductive amination forms a reduced hydrazone.

It is an advantage of the present invention to provide an improved antithrombogenic polymer coating that may be easily applied to a substrate to provide a material which has excellent biological and chemical stability towards blood and which retains its antithrombogenic properties in a permanent and non-leachable fashion when in contact with blood for prolonged periods.

It is another advantage of the invention to provide a process for the preparation of a two-dimensional-polymer surface containing pendant reactive hydrazide groups that may be further attached to an antithrombogenic agent such as heparin.

It is yet another advantage to provide a process for the preparation of a two-dimensional-polymer surface containing pendant reactive hydrazide groups that is easily realized by coupling the polymer with a crosslinking agent in the presence of a linking agent (i.e., spacer-arm) containing at least two hydrazide groups wherein the intermediary layer from the copolymer thus obtained demonstrates excellent ability to form a stable linkage with the substrate while leaving its pendant hydrazide groups for further attachment to an antithrombogenic agent such as heparin.

It is still another advantage to provide a process for immobilizing heparin to a reactive coating surface and to provide a process for multiplication of reactive sites through activation of NH$_2$—, NH—, or hydrazide groups on the coating surface followed by coupling with a trihydrazide or polyhydrazide.

These and other features, aspects, and advantages of the present invention will become better understood upon consideration of the following detailed description, drawings, and appended claims.

BRIEF DESCRIPTION OF THE DRAWINGS

FIGS. 2A and 2B show a process for synthesizing another example polyamide having amino groups that are suitable for forming the antithrombogenic polymer coating in accordance with the present invention.

DETAILED DESCRIPTION OF THE INVENTION

An article having a non-thrombogenic surface according to the invention comprises a substrate, a coating disposed on at least a portion of the substrate, and an antithrombogenic agent covalently bonded to the coating. The coating comprises a crosslinked chemical combination of (i) a polymer having side chains along a backbone forming the polymer, at least two of the side chains containing an amino group, (ii) a crosslinking agent containing at least two functional groups capable of reacting with the amino groups, and (iii) a linking agent containing a first functional group and a second functional group, the first functional group capable of reacting with a third functional group of the crosslinking agent. The antithrombogenic agent is covalently bonded to the second functional group of the linking agent.

It has been discovered that an antithrombogenic agent, such as heparin, may be readily attached to a two-dimensional polymer bearing side chains having hydrazide groups. Two-dimensional polymers bearing different hydrazide side chains are readily obtainable through crosslinking between the two-dimensional polymer with a crosslinking agent and a hydrazide linking agent (spacer arm) carrying at least two hydrazide groups. A tri-block composite solution containing a two-dimensional polymer, a polyhydrazide and a crosslinking agent is used directly, without isolation of the product, for the coating of a substrate. The best performance for the invention may be attained by the selection of proper reagents and optimum reaction conditions.

Figure 1A:
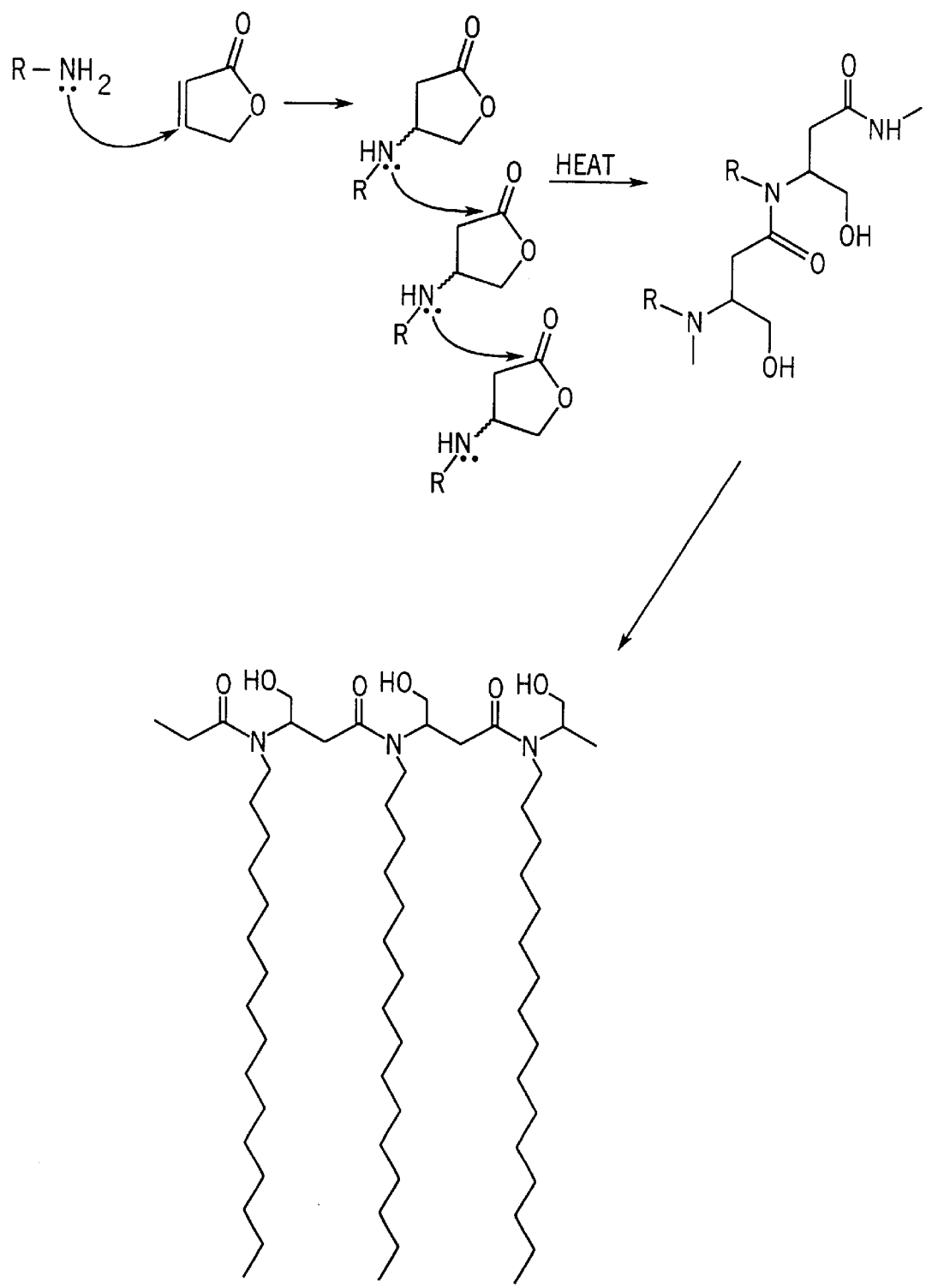
FIG. 1A shows a process for synthesizing a polyamide that is suitable for forming an antithrombogenic polymer coating in accordance with the present invention.
Figure 1B:
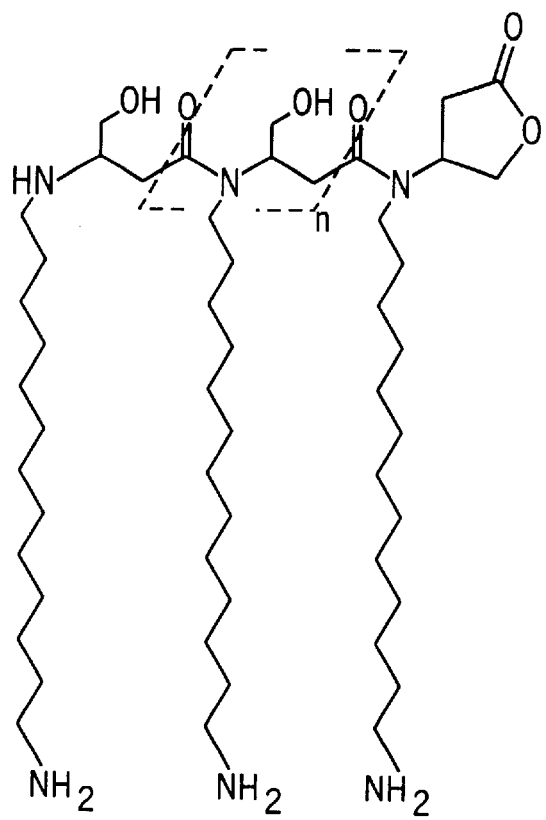
FIG. 1B shows example polyamides having amino groups that are suitable for forming the antithrombogenic polymer coating in accordance with the present invention.
Figure 1B:
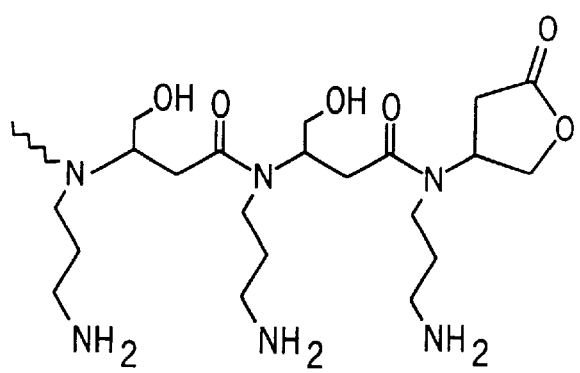

The polymer used in the coating comprises a polymer having side chains along a backbone forming the polymer wherein at least two of the side chains contain an amino group (—NRH, —NH$_2$, —NRH$_2^+$, —NH$_3^+$). In one example embodiment of the polymer, the polymer is a polyamide synthesized using the polymerization reactions disclosed in PCT International Publication Number WO 00/17254, which are shown in FIG. 1A. Looking at FIG. 1A, it can be seen that the polyamide can be synthesized using an α, β-unsaturated gamma-lactone, such as 2(5H)-furanone, as an agent to effect the regular, sequential alignment of side chains along a polyamide backbone. The furanone undergoes facile reaction with a primary amine by Michael-type addition to yield α,β-amino gamma-lactone which then polymerizes to form a polyamide chain with the pendant side chain. Depending on the side group (R), the method can produce many different types of polyamides. When the R group is a polyamine (such as pentaethylenehexamine), a polymer having alkyl chains on one side and amino substituted alkyl chains on the other side of the polymer backbone and hydroxymethyl groups on the other side of the backbone is formed. See FIG. 1B. This example two-dimensional polymer has a backbone of repeating β-amino acid units with fatty alkyl (tetradecyl) and polyamine (derived from pentaethylenehexamine) side chains randomly distributed along the chain. By virtue of its amphithetic properties, the two-dimensional polymers are easily soluble in both water and most organic solvents (e.g., alcohols, tetrahydrofuran, chloroform, toluene, N,N-dimethylformamide, and the like).

One polyamide disclosed in PCT International Publication Number WO 00/17254 and useful in the present invention is formed by reacting an α,β-unsaturated lactone and a first amine to form an intermediate reaction product, wherein the first amine is selected from RR$_1$NH, RNH$_2$, RR$_1$NH$_2^+$, RNH$_3^+$ and mixtures thereof, wherein R and R$_1$ can be the same or different and each contain between about 1 and 50 carbon atoms and are optionally substituted with heteroatoms oxygen, nitrogen, sulfur, and phosphorus and combinations thereof; and (ii) reacting the intermediate reaction product and a polyamine to form the polyamide, wherein the second polyamine is selected from R$_2$R$_3$NH, R$_2$NH$_2$, R$_2$R$_3$NH$_2^+$, R$_2$NH$_3^+$ and mixtures thereof, wherein R$_2$ and R$_3$ can be the same or different and each contain an amino group (—NRH, —NH$_2$, —NRH$_2^+$, —NH$_3^+$) and between about 1 and 50 carbon atoms and are optionally substituted with heteroatoms oxygen, nitrogen, sulfur, and phosphorus and combinations thereof, wherein multiple of the R, $R_1$, $R_2$, and $R_3$ are in vertically aligned spaced relationship along a backbone formed by the polyamide. In one example embodiment of the invention, R, $R_1$, $R_2$, and $R_3$ may be selected from alkyl, alkenyl, alkynyl, cycloalkyl, aryl, aralkyl, hydroxyl, nitrile, carboxyl, sulfate, phosphate, sulfonyl, trialkylammonium and combinations thereof and optionally can be substituted with a halogen selected from the group consisting of chlorine, iodine, bromine, fluorine and combinations thereof. The R, $R_1$, $R_2$, and $R_3$ groups may be the same or different depending on the desired structure for the final polyamide. In other words, the first amine and the second amine used in the polymerization process may be the same or different.

Figure 2B:
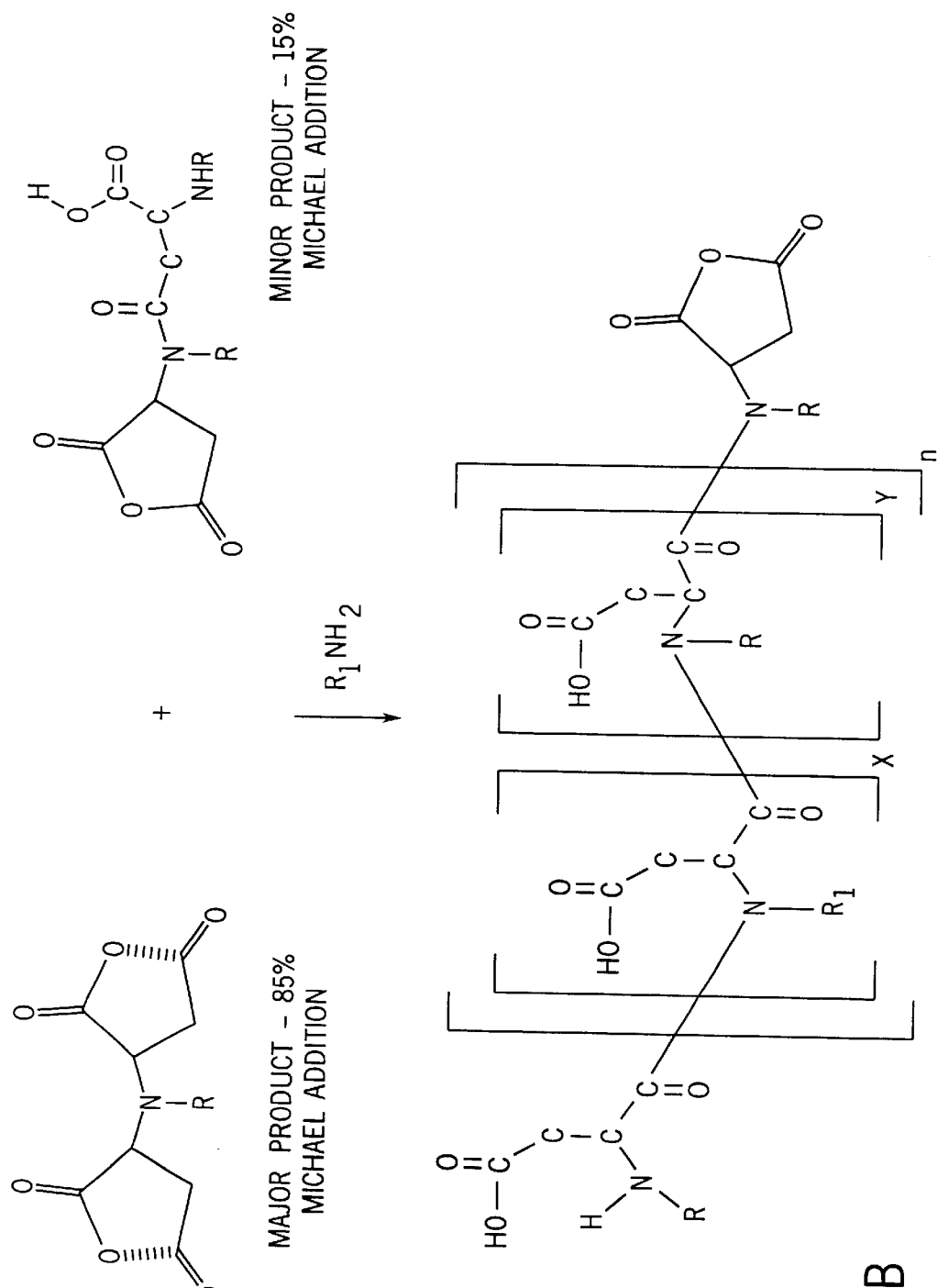

In another example of the polymer used in the coating, the polymer is a polyamide synthesized using the polymerization reaction disclosed in the U.S. Patent Application entitled "Two Dimensional Polyamides Prepared from Unsaturated Carboxylic Acids and Amines" filed on Oct. 27, 2000 by William F. McDonald et al., which is owned by the assignee of the present invention and is incorporated herein by reference. In the U.S. Patent Application, there is described a polymerization process in which a monomer selected from unsaturated carboxylic acids, esters of unsaturated carboxylic acids, anhydrides of unsaturated carboxylic acids, and mixtures thereof is reacted with a first amine to form an intermediate reaction product, and then the intermediate reaction product is reacted with a polyamine to form a polyamide wherein at least a portion of the side chains along a backbone forming the polyamide are amino substituted alkyl chains. See FIGS. 2A and 2B (wherein $R_1$ includes an amino group).

The process for producing this polyamide involves reacting a monomer selected from unsaturated carboxylic acids, esters of unsaturated carboxylic acids, anhydrides of unsaturated carboxylic acids and mixtures thereof with a first amine to form an intermediate reaction product in the reaction mixture, wherein the first amine is selected from $RR_1NH$, $RNH_2$, $RR_1NH_2^+$, $RNH_3^+$ and mixtures thereof, wherein R and $R_1$ can be the same or different and each contain between about 1 and 50 carbon atoms and are optionally substituted with heteroatoms oxygen, nitrogen, sulfur, and phosphorus and combinations thereof. The reaction of the monomer and the first amine forms an intermediate reaction product in the reaction mixture. The intermediate reaction product is then reacted with a second amine selected from $R_2R_3NH$, $R_2NH_2$, $R_2R_3NH_2^+$, $R_2NH_3^+$ and mixtures thereof, wherein $R_2$ and $R_3$ can be the same or different and each contain an amino group (—NRH, —$NH_2$, —$NRH_2^+$, —$NH_3^+$) and each contain between about 1 and 50 carbon atoms and are optionally substituted with heteroatoms oxygen, nitrogen, sulfur, and phosphorus and combinations thereof. The reaction of the intermediate reaction product with the second amine forms the polyamide in the reaction mixture. The polyamide may then be separated from the reaction mixture. A polyamide produced in accordance with the method of the invention includes multiples of the R, $R_1$, $R_2$, and $R_3$ groups in vertically aligned spaced relationships along a backbone formed by the polyamide.

Suitable unsaturated carboxylic acids, esters of unsaturated carboxylic acids, and anhydrides of unsaturated carboxylic acids for use as the monomer in this polymerization process have for example from 3 to 18 carbon atoms in the molecule. Of this group of acids, the monocarboxylic acid, acrylic acid, and the dicarboxylic acid, maleic acid, are preferred. Of this group of esters, maleic acid monoesters are preferred. A non-limiting example of anhydrides of the unsaturated carboxylic acids is maleic anhydride. In one example embodiment of the invention, R, $R_1$, $R_2$, and $R_3$ may be selected from alkyl, alkenyl, alkynyl, cycloalkyl, aryl, aralkyl, hydroxyl, nitrile, carboxyl, sulfate, phosphate, sulfonyl, trialkylammonium and combinations thereof and optionally can be substituted with a halogen selected from the group consisting of chlorine, iodine, bromine, fluorine and combinations thereof. The R, $R_1$, $R_2$, and $R_3$ groups may be the same or different depending on the desired structure for the final polyamide. In other words, the first amine and the second amine used in the polymerization process may be the same or different.

The crosslinking agent used in the coating contains at least two functional groups capable of reacting with the amino groups of the polymer used in the coating. It has been discovered that the polymer can be crosslinked using a phosphine crosslinking agent having the general formula $(A)_3P$ and mixtures thereof, wherein A is hydroxyalkyl. The A groups of the phosphine crosslinking agent undergo a spontaneous Mannich-type reaction with amino groups on the polymer under mild conditions (pH ~7, aqueous or organic media, room temperature, 2–24 hours). This results in the formation of an aminomethyl-phosphine linkage (N—$CH_2$—P—$CH_2$—N) which is much less susceptible to enzyme deactivation and hydrolysis at a low pH than other known crosslinkages. In addition, the phosphine crosslinking agent offers the benefits of operational simplicity, good biocompatibility, and low cost. The phosphine crosslinking agent can also react with the substrate to create tightly bound anchors between the polyamide coating and the substrate. Non-limiting examples of phosphine crosslinking agents include tris(hydroxymethyl)phosphine, tris(1-hydroxyethyl) phosphine, and tris(1-hydroxypropyl)phosphine.

The amount of phosphine crosslinking agent and the amount of polymer used in the crosslinking process can be varied depending upon the particular crosslinking agent utilized, the reaction conditions and the particular product application contemplated. Typically, the ratio of A groups in the phosphine crosslinking agent to the total of amount of amino groups in the polyamide can be varied to achieve a predetermined level of crosslinking. Typically, the A groups in the phosphine crosslinking agent to the total of amount of amino groups in the polymer is about 30% to provide acceptable crosslinking. In one version of the invention, enough phosphine crosslinking agent is added to the polyamide such that at least 30% of the available amino groups in the polymer are crosslinked by the A groups in the phosphine crosslinking agent. This percentage or amount of phosphine crosslinker can be varied to obtain coatings with the desired crosslink density.

The linking agent used in the coating contains a first functional group capable of reacting with a third functional group in the crosslinking agent and a second functional group capable of reacting to form a covalent bond with the antithrombogenic agent, such as heparin. It was determined that the stability of immobilized heparin and other biomolecules is greatly dependent on the length and the lipophilicity of the linking agent and the number of active groups it contains. As a result, it has been discovered that a linking agent having at least two hydrazide groups (—$CONHNH_2$) is capable of reacting with a functional group in the crosslinking agent and the antithrombogenic agent, and is beneficial when used in the present invention. A first hydrazide group of the linking agent can react and covalently combine with an A (i.e., hydroxyalkyl) group in the phosphine crosslinking agent described above, and a second hydrazide group of the linking agent can react and combine covalently with the antithrombogenic agent (e.g., heparin). Typically, the second hydrazide group covalently bonds with the antithrombogenic agent (e.g., heparin) at its reducing end. Accordingly, the linking agent may be a polyhydrazide, and may be selected from the following non-limiting examples of polyhydrazides: carbohydrazide, thiocarbohydrazide, adipic dihydrazide, azelaic dihydrazide, sebacic dihydrazide, isophthaloyl dihydrazide, terephthaloyl hydrazide, 2,6-naphthalenedicarboxylic dihydrazide, 4,4'-O-bis(benzoyl hydrazide), 4,4'-O-bis(benzenesulfonyl hydrazide), citric trihydrazide, 1,3,5-benzenetricarbonyl hydrazide, poly(methacrylyl hydrazide), poly(methacrylyl ADP), poly(methyl vinyl ether-alt-maleic hydrazide), poly (methyl vinyl ether-alt-maleic ADP), poly(isobutylene-alt-maleic anhydride), poly(1-tetradecene-alt-maleic anhydride), poly(1-octadecene-alt-maleic anhydride), poly ($\alpha$-$C_{24}$-$C_{28}$ olefin-maleic anhydride), dendritic hydrazides synthesized from trihydrazides (e.g., citric trihydrazide (CTH), 1,3,5-benzenetricarbonyl trihydrazide (BTH)) and tris(hydroxymethyl)phosphine (THP) such as THP+CTH and THP+BTH ($1^{st}$ generation, contains 6 terminal hydrazides) and THP+CTH and THP+BTH ($2^{nd}$ generation, contains 12 terminal hydrazides), and mixtures thereof.

The antithrombogenic agent may be any material which inhibits thrombus formation on its surface (such as by reducing platelet aggregation, dissolving fibrin, enhancing passivating protein deposition, or inhibiting one or more steps within the coagulation cascade) and which is capable of forming a covalent bond with a functional group (e.g., hydrazide) on the linking agent. Illustrative antithrombogenic agents may be selected from the group consisting of heparin, prostaglandins, urokinase, streptokinase, sulfated polysaccharide, albumin and mixtures thereof. In an example embodiment of the invention, the antithrombogenic agent is heparin. The antithrombogenic agent may be used in varying amounts depending on the particular material employed and ultimate desired effect. For instance, the preferred heparin level is about 0.5% by weight and may range from about 0.1% by weight to about 1.0% by weight.

The substrate of an article according to the invention may comprise any polymeric material conventionally used to fabricate articles commonly used in contact with blood. A suitable polymeric material may be selected from polyolefins, polyacrylics, polyvinyl chloride, polyamides, polyurethanes, polyurethaneureas, silicone urethane copolymers, polyvinylpyrrolidone, polyvinyl alcohols, cellulosic materials, polystyrene, polyesters, fluorinated polymers, silicone polymers, natural rubber, polycarbonates, and mixtures thereof. The particular substrate selected does not constitute a critical aspect of the invention other than to serve as a support substrate for the coating and the antithrombogenic agent. In other words, the substrate must be able to bond to the polymer coating.

An article having a non-thrombogenic surface according to the invention may be prepared generally as follows. First, the substrate is precleaned, if necessary, and the surface of the substrate is modified, if necessary. A solution of the polymer having side chains along a backbone forming the polymer wherein at least two of the side chains contain an amino group (—NRH, —$NH_2$, —$NRH_2^+$, —$NH_3^+$), the crosslinking agent, and the linking agent is then prepared. Typically, the polymer may be dissolved using polar solvents, followed by addition of the crosslinking agent and the linking agent to form a coating solution. Care is taken not to heat this solution as premature crosslinking is undesirable. The polymer/crosslinking agent/linking agent solution is applied to a substrate and the substrate may be heated or baked in an oven at 125° C. for four hours to complete the crosslinking process and create a crosslinked polymer coating having pendant reactive groups on the substrate. Thereafter, the coating on the substrate is heparinized or treated with another antithrombogenic agent which is capable of forming a covalent bond with a functional group on the linking agent.

One example process for producing an article having a non-thrombogenic surface according to the invention proceeds as follows. A polydimethylsiloxane substrate is precleaned using a one time isopropanol rinse. The substrate surface is modified by dipping the substrate in 1 to 2% [2-(2-aminoethylamino) ethylamino] propyltrimethoxysilane and 0.2% acetic acid in isopropanol and thereafter drying the substrate with hot air. This step may be repeated if necessary. A solution of a polyamide (which may be synthesized using the polymerization reactions disclosed in PCT International Publication Number WO 00/17254 to have amino substituted alkyl chains on the polymer backbone), a crosslinking agent (such as tris (hydroxymethyl)phosphine), and a linking agent (such as adipic dihydrazide) is then prepared to react the polyamide, the crosslinking agent, and the linking agent. For example, 100 milliliters of 2% polyamide is mixed with 0.5 grams of tris(hydroxymethyl)phosphine and 0.5 grams of adipic dihydrazide. The reaction between the polyamide, the crosslinking agent, and the linking agent can be conducted in aqueous and organic phases. Considering the solvent ability, the compatibility with the substrate and reagents, the boiling point, the miscibility with other solvents, and safety factors, isopropanol is one preferred solvent for the crosslinking and subsequent coating procedure. However, 1-methoxy-2-propanol and tetrahydrofuran are sometimes used as co-solvents for improved solubility. In order to provide a smooth crosslinking under optimum stoichiometry, an example concentration ratio for the reactants is: Polymer: Linking agent: Crosslinking agent=2:0.5:0.5 w/w % (1:0.25:0.25 w/w %). This corresponds roughly to a ratio of 1:1.5 (molar) for adipic dihydrazide vs. tris(hydroxymethyl) phosphine. Increasing adipic dihydrazide concentration may be difficult because of poor solubility. Higher concentrations of tris(hydroxymethyl)phosphine may lead to an extremely short pot life by precipitation of the crosslinked materials from solution. Accordingly, a suitable concentration ratio for the reactants is: Polymer:Linking agent:Crosslinking agent= 1000 milligrams:50 milligrams:440 milligrams.

The polymer solution is applied to the substrate by dipping the substrate in the solution and thereafter drying the substrate with hot air. This step may be repeated if necessary. The coated substrate is then successively washed with phosphate buffer (pH 7.4), and distilled water. Surface functionalization resulting in either imbedded or surface-coated hydrazides can be verified by a 2,4,6-trinitrobenzenesulfonic acid test (described by T. Miron and M. Wilchek, in *J. Chromatogr.* 215, 55–63, 1981, and by J. K. Inman, B. Merchant, and S. E. Tacey in *Immunochemistry* 10, 153–163, 1973) by which the degree of incorporation is indicated by the color change (from pale yellow to deep orange). Fourier Transform Infrared Spectroscopy (FT-IR) may also be performed with FT-IR at 3292, 2922, 1645 and 1258 (Si—$CH_3$) for the coating and polydimethylsiloxane. The coated substrate having hydrazide groups may then be heparinized by immersing in a heparin sodium salt solution 0.5% in 50 mM citrate phosphate buffer, pH 5 for 1 hour, or immersing in a heparin sodium salt (0.5%) and $NaBH_3CN$ (0.17%) solution in 50 mM citrate phosphate buffer, pH 5) for 1 hour. The heparinized substrate is then successively washed with a phosphate buffer, pH 7.4, and water. A toluidine blue (in borate, pH 9) assay test may then be performed for quantifying the surface heparin content of the heparinized substrate. The heparinized substrate may then be subjected to an accelerated 5 day coating stability study. The coated substrate is immersed in phosphate buffered saline at a pH=5 and 7.4 at both 25° C. and 37° C. The coated substrates were held at pH=5 for 5 days with no detectable change in the heparin loading. Another group of heparinized coated substrates were immersed in pH 7.4 phosphate buffered saline for 15 days with no detectable changes.

EXAMPLES

The following examples serve to further illustrate the invention. Example 1 details the preparation of polyhydrazides suitable for use as the linking agent in the present invention. Example 2 details the preparation of hydroxyalkyl substituted phosphines suitable for use as the crosslinking agent in the present invention. Example 3 illustrates the preparation of a triblock crosslinked polyamide surface having pendant reactive hydrazide groups in accordance with the invention. Example 4 illustrates the preparation of another triblock crosslinked polyamide surface having pendant reactive hydrazide groups in accordance with the invention. Example 5 illustrates the heparinization of a triblock crosslinked polyamide surface having pendant reactive hydrazide groups in accordance with the invention. The examples are not intended to limit the invention in any way.

Example 1

Preparation of Hydrazides

Example 1a

Citric trihydrazide was prepared as follows. A 4.5 milliliter sample (4.5 grams, 91.7 mmol) of hydrazine hydrate was added to a solution of 5.70 grams (5 milliliters, 20.5 mmol) of triethyl citrate in 50 milliliters absolute ethanol. After stirring at room temperature for 8 hours, the solution was poured into a mortar while allowing the solvent to evaporate for overnight under a hood. The resulting white crystalline product was ground in mortar, washed with about 50 milliliters of ethanol, filtered, and air-dried. The yield was 4.60 grams (95.5% of theoretical). MALDI-MS showed [M+H]$^+$ at m/z 249 (matrix: 4-hydroxy-α-cyanocinnamic acid).

Example 1b 1,3,5-benzenetricarbonyl trihydrazide was prepared as follows. To 5.0 grams of 1,3,5-benzenetricarbonyl chloride (18.86 mmol) suspended in 50 milliliters isopropanol was added dropwise 3.5 milliliters (70 mmol) hydrazine hydrate for 15 minutes under stirring. The mixture was then allowed to stand for overnight to leave a white product, which was finally ground in a mortar to provide a fine powder. The product was filtered and air-dried. The yield was 4.61 grams (96.5% of theoretical).

Example 1c

Poly(1-octadecene-alt-maleic acid hydrazide) (POMAH) was prepared as follows. To 8.2 grams (23.4 milli-equivalent units) of poly(1-octadecene-alt-maleic anhydride) (POMA) (available from Aldrich Chemical, $M_n$ 30–50 k) in 100 milliliters 1:1 (v/v) toluene-isopropanol was added 4.1 milliliters (84.5 mmol) hydrazine hydrate. The solution was stirred at room temperature for 24 hours (a white precipitate was formed after several hours). A mixture of 50 milliliters isopropanol and 3 milliliters of acetic acid was then added to complete the precipitation. The product was vacuum filtered, washed with 3×50 milliliters methanol to remove any unreacted hydrazine. The polyhydrazide, 8.0 grams (97.5% of theoretical), was obtained as a white powder after drying overnight in a desiccator over $P_2O_5$. FT-IR showed: 2916 (strong, $CH_2$ stretching), 2848 ($CH_2$ stretching), 1727 (very strong, cyclic hydrazide carbonyl C=O stretching), 1463 ($CH_2$, long chain CH bending), 1253 (cyclic C—N stretching), 1172 (cyclic amide C—N stretching/bending), and 1139 (C—N stretching) cm$^{-1}$. The absorption bands due to cyclic anhydride were eliminated or significantly reduced. These peaks included 1885, 1776 (strong-anhydride C=O), 1219 and 922 (C—O—C for 5 membered ring). They were visible in the starting material, but not seen in the polyhydrazide product.

Example 2

Preparation of tris(hydroxymethyl)phosphine

Tris(hydroxymethyl)phosphine (THP) was prepared from tetrakis-(hydroxymethyl)phosphonium chloride (THPC) as follows. Eighteen milliliters (corresponding to 19.3 grams anhydrous, or 101.5 mmol) 80% THPC was mixed with 100 milliliters isopropanol and 50 milliliters toluene. The mixture was evaporated to dryness on a Rotavap (bath temperature 80–90° C.), and the azeotropic distillation was repeated for 2 more times to provide a semi-solid mass of anhydrous THPC. The dried residue was dissolved in 60 milliliters of isopropanol, to which was added 40 milliliters dry triethylamine (TEA) under ice-cooling. After the exothermic reaction had subsided, the mixture was set in a freezer (–10° C.) for 1 hour to ensure that the precipitation of TEA.HCl was completed. The TEA salt was filtered off, and the filtrate was allowed to evaporate to dryness. Heating under reduced pressure on the Rotavap (bath temperature 80–90° C.) was continued for 4 hours to give a clear viscous liquid. The yield of THP was 11.8 grams (94% of theoretical). EIMS (electron ionization mass spectroscopy, direct inlet) exhibited a molecular ion at m/z 124 together with fragments at m/z 106, 94, 76, 64, 61, 46, and 31, formed due to successive loss of $H_2O$, and $CH_2O$ from the molecular ion. Infrared absorptions occur at 3224 (broad), 2815, 1589, 1420, 1125 (strong), and 1030 (strong) cm$^{-1}$. The THP thus prepared is pure enough for use in crosslinking. It is relatively stable and can be stored in freezer for up to 8 weeks without noticeable decomposition. Further purification of THP by distillation is not recommended due to thermal decomposition above 130° C. releasing $PH_3$ gas in the process.

Example 3

Preparation of a Triblock Polymer Surface

Example 3a

Preparation of a Polymer with Side Chains

The procedure described in Example 16 of WO 00/17254 was used to produce a polyamide with mixed side chains. This polymer was produced by adding 1 molar equivalent of furanone (2(5H)-furanone) to 50 milliliters isopropanol, followed by adding 0.5 molar equivalents of tetradecylamine to the furanone solution dropwise. Once the tetradecylamine addition is complete, 0.25 molar equivalents of pentaethylenehexamine is added. The polymer produced had the mixed side chains and is suitable for making coatings. This polymer had a structure analogous to those shown in FIG. 1B.

Example 3b

Preparation of a Polymer Surface from a Polymer Having Side Chains

A triblock polymer surface was prepared from the polymer prepared in Example 3a by crosslinking with tris (hydroxymethyl)phosphine (prepared in Example 2—THP) as follows. Four hundred twenty milligrams (2.41 mmol) of a fine powder of adipic dihydrazide (ADH) was mixed (under stirring) with a solution of 50 milliliters of 2% polymer of Example 3a (~4 milliequivalent units) in isopropanol. After 10 minutes, 300 milligrams (2.41 mmol) of THP was added in one portion. Stirring was continued for 0.5 hours to enable maximum dissolution. Any insoluble material (e.g., 50–120 milligrams unreacted ADH recovered) is filtered off to leave a clear yellow solution. This solution remains clear for 4–8 hours. (However, for obtaining high quality coatings, it is recommended to use a fresh solution prepared within 2 hours). This triblock composite solution was applied to a polydimethylsiloxane and a polypropylene substrate material. In doing so, the substrate was dipped into the solution and removed after 0.5 to 2 minutes. The wet substrate was dried and cured by hot air at 120° C.–150° C. for 1 minute. The dip-and-dry operation can be repeated one or more times when a greater thickness is required. Finally, the coated article was incubated in 50 mM phosphate buffer at pH 7.4 (15 minutes) and rinsed with running distilled water to remove any loosely bonded material yielding a glassy coated surface. Surface hydrazide was detected by dipping a sample into a 1% aqueous solution of 2,4,6-trinitrobenzenesulfonic acid to develop a faint yellow to deep orange coloration, depending on the abundance of the hydrazide function. FT-IR exhibited characteristic bands (cm$^{-1}$) at 3292 (NH/OH, broad), 2922 (CH$_2$/CH for long fatty chain), 1774 (C=O), 1645 (amide I strong), 1558 (amide II), 1461 (CH$_2$/CH), and 1258 (sharp, Si—CH$_3$). The ratio of absorbance A2922/A1258 or A1645/A1258 was used as a measure for the surface thickness and homogeneity in quality control.

Example 3c

Preparation of a Polymer Surface from a Polymer Having Side Chains

Another triblock polymer surface was prepared from the polymer prepared in Example 3a by crosslinking with tetrakis(hydroxymethyl)phosphonium chloride (THPC) as follows. Four hundred twenty milligrams (2.41 mmol) of a fine powder of adipic dihydrazide (ADH) was mixed (under stirring) with a solution of 50 milliliters of 2% polymer of Example 3a (~4 milliequivalent units) in isopropanol. After 10 minutes, 0.45 milliliters of 80% THPC (2.5 mmol) and 0.35 milliliters (2.5 mmol) of triethylamine were added in one portion. Stirring was continued for 0.5 hours to enable maximum dissolution. Any insoluble material (e.g., 50–120 milligrams unreacted ADH recovered) is filtered off to leave a clear yellow solution. This solution remains clear for 4–8 hours. (However, for obtaining high quality coatings, it is recommended to use a fresh solution prepared within 2 hours). This triblock composite solution was applied to a polydimethylsiloxane and a polypropylene substrate mate-rial. In doing so, the substrate was dipped into the solution and removed after 0.5 to 2 minutes. The wet substrate was dried and cured by hot air at 120° C.–150° C. for 1 minute. The dip-and-dry operation can be repeated one or more times when a higher thickness is required. Finally, the coated article was incubated in 50 mM phosphate buffer at pH 7.4 (15 minutes) and rinsed with running distilled water to remove any loosely bonded material yielding a glassy coated surface. Surface hydrazide was detected by dipping a sample into a 1% aqueous solution of 2,4,6-trinitrobenzenesulfonic acid to develop a faint yellow to deep orange coloration, depending on the abundance of the hydrazide function.

Example 4

Preparation of Another Triblock Polymer Surface

Example 4a

Preparation of Another Polymer with Side Chains

Another polymer with side chains was prepared as follows. First, 1.0 moles (144.1 grams) of maleic acid monoethyl ester (MAEE) was dissolved in 100 grams of isopropanol in a break away resin kettle. The kettle containing the MAEE/isopropanol solution was then cooled in an ice bath with agitation. Second, 0.5 moles (160.7 grams) of commercially available tetradecylamine was dissolved in 250 grams of isopropanol and added slowly to the cooled MAEE solution with stirring. A Michael-type addition reaction product began to precipitate within 5 minutes. The tetradecylamine addition required about two hours with ice bath conditions being maintained throughout. Third, 58.1 grams (0.25 moles) of commercially available pentaethylenehexamine (PEHA) were added drop wise to the reaction solution over a two hour period. The reaction is removed from the ice bath at the end of the monomer addition and stirred for an additional 2 hours. The amount of PEHA charged is determined from the monomer charge from the formation of intermediate. After complete addition of the PEHA, the reaction kettle was removed from the cold bath with continuous stirring for another 2 hours.

Example 4b

Preparation of Triblock Polymer Surface from Example 4a Polymer

To 50 milligrams of finely ground poly(1-octadecene-alt-maleic acid hydrazide) (POMAH) and 20 milligrams Triton X-100 brand surfactant were added 10 milliliters each of tetrahydrofuran and 1-methoxy-2-propanol. After stirring for 10 minutes at room temperature, the suspension was mixed with 25 milliliters 3% (w/w) of the polymer of Example 4a in isopropanol. Stirring was continued for 10 more minutes to ensure complete dissolution. Thereafter, 440 microliters of 80% THPC and 500 microliters of TEA were introduced dropwise to the solution under stirring. The mixture was filtered after 15 minutes to obtain a clear, yellow solution for use in coating. This triblock composite solution was applied to a polydimethylsiloxane and a polypropylene substrate material. In doing so, the substrate was dipped into the solution and removed after 0.5 to 2 minutes. The wet substrate was dried and cured by hot air at 120° C.–150° C. for 1 minute. The dip-and-dry operation can be repeated one or more times when a higher thickness is required. Finally, the coated article was incubated in 50 mM phosphate buffer at pH 7.4 (15 minutes) and rinsed with running distilled water to remove any loosely bonded material yielding a glassy coated surface. Surface hydrazide was detected by dipping a sample into a 1% aqueous solution of 2,4,6-trinitrobenzenesulfonic acid to develop a faint yellow to deep orange coloration, depending on the abundance of the hydrazide function. Infrared analysis of the resulting coated polydimethylsiloxane articles showed characteristic absorbances at 3300 (NH), 2922 ($CH_2$/CH), 2850, 1650 (amide 1), and 1258 (Si—$CH_3$ of siloxane substrate) $cm^{-1}$.

Example 5

Heparinization of Triblock Polymer Surface

Example 5a

Direct heparinization with sodium heparin (Hydrazone formation)

The polymer coated articles prepared in Examples 3b, 3c and 4b were allowed to incubate in a solution of 0.5% sodium heparin in 50 mM phosphate buffer at pH 5 at room temperature for 1 hour. The products were rinsed with (i) distilled water, (ii) 50 mM phosphate buffer at pH 7.4 (15 minutes), and (iii) distilled water, and finally air-dried overnight.

Example 5b

Heparinization by Reductive Amination (Formation of Reduced Hydrazone)

The polymer coated articles prepared in Examples 3b, 3c and 4b were allowed to incubate in a solution of 0.5% sodium heparin and 0.17% $NaBH_3CN$ (heparin: $NaBH_3CN$= 3:1 w/w) in 50 mM phosphate, pH 5, at room temperature for 1 our. The products were rinsed with (i) distilled water, (ii) 0.5 mM phosphate buffer at pH 7.4 (15 minutes), (iii) distilled water, and finally air-dried overnight. This washing step removed the last trace of $CN^{-1}$ ions as indicated by the absence of bands at 2328 ($CN^{-1}$-metal coordinated) and 2168 ($CN^{-1}$) in an FT-IR infrared spectrum.

Example 5c

Toluidine Blue Assay

The surface bonded heparin of the articles produced in Examples 5a and 5b was analyzed by the toluidine blue (basic) test described by B. Dick et al. in *Ophthalmologica* 211, 75–78, 1997 and by L. B. Jaques in *Methods of Biochem. Anal.* v. 24 (D. Glick, ed.), pp. 241–243, Wiley & Sons, New York, 1977, by which the analyte was allowed to react with an excess of toluidine blue to form an insoluble heparin-cationic dye complex and the depleted dye was analyzed by measuring the UV-absorption at 631 nanometers. A mixture of 20 milligrams of toluidine blue, 50 milliliters of 0.025 M sodium borate, and 4.6 milliliters of 0.1 N HCl was diluted to 100 milliliters with water to form 0.02% (or 200 mg/L) toluidine blue in 0.0125 M sodium borate (pH 9.0). Then 16.6 milligrams of sodium heparin was dissolved in 100 milliliters of 0.2% NaCl to form a heparin solution (6.0 micrograms heparin/microliter solution). A sample of 1.0 milliliters of the toluidine blue reagent was added to each labeled centrifuge tube (15 milliliters) for standards and unknowns. Then 0, 25, 50, 75, and 100 micrograms of sodium heparin were added to each standard tube. Then 0.2% NaCl was added to each heparin and unknown tube to 5.0 milliliters.

Heparinized samples from Examples 5a and 5b were added in small pieces to the tubes designated unknowns. One milliliter of hexane was added to each tube to promote the separation of unbound heparin-dye complex at the interface. The tubes were vortexed 3 times for 2 minutes each time and allowed to stand at room temperature for 2 hours. The lower layer was transferred from each tube to a 0.5-milliliter disposable cuvette and the absorption at 631 nanometers was recorded. A plot was then made of the average absorbance vs. concentration of the triplicate standard heparin solutions. The heparin concentration of the unknowns was determined by comparing the $A_{631}$ values against the standard curve. This protocol offers advantages over other procedures using acidic toluidine blue (such as that described by P. K. Smith, A. K. Mallia, and G. T. Hermanson in *Anal Biochem.* 109, 466–473, 1980) because it is insensitive to the charge present on the polydimethylsiloxane substrate surface and does not give false positive responses in the presence of polymers of Examples 3a and 4a as analyzed in acidic media. The assay showed that heparin was present on the surface of the articles produced in Examples 5a and 5b at a concentration of about 5 to about 10 micrograms per square centimeter.

Therefore, it can be seen that this work has provided an improved antithrombogenic polymer coating that may be easily applied to a substrate to provide a material which has excellent biological and chemical stability towards blood and which retains its antithrombogenic properties in a permanent and non-leachable fashion when in contact with blood for prolonged periods. The process provides for the preparation of a two-dimensional-polymer surface containing pendant reactive hydrazide groups that may be further attached to an antithrombogenic agent such as heparin. The process also provides for the preparation of a two-dimensional-polymer surface containing pendant reactive hydrazide groups that is easily realized by coupling the polymer with a crosslinking agent in the presence of a linking agent (i.e., spacer-arm) containing at least two hydrazide groups wherein the intermediary layer from the copolymer thus obtained demonstrates excellent ability to form a stable linkage with the substrate while leaving its pendant hydrazide groups for further attachment to an antithrombogenic agent such as heparin.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A process for rendering the surface of a substrate non-thrombogenic, the process comprising:
    (a) providing a polymer having side chains along a backbone forming the polymer, at least two of the side chains containing an amino group;
    (b) mixing the polymer with a crosslinking agent and a linking agent to produce a polymer solution, the crosslinking agent containing at least two crosslinking functional groups that react with the amino groups, and the linking agent containing a first functional group and a second functional group, the first functional group reacting with a third functional group of the crosslinking agent;
    (c) providing a substrate;
    (d) coating at least a portion of the substrate with the polymer solution to produce a crosslinked polymer coating on the substrate; and (e) contacting at least a portion of the crosslinked polymer coating on the substrate with an antithrombogenic agent whereby the antithrombogenic agent covalently bonds to the second functional group of the linking agent.

2. The process of claim 1 wherein the first functional group and the second functional group of the linking agent have the formula —CONHNH$_2$.

3. The process of claim 2 wherein the crosslinking agent is selected from the group consisting of phosphines having the general formula (A)$_3$P, wherein A is hydroxyalkyl.

4. The process of claim 1 wherein the crosslinking agent is selected from the group consisting of phosphines having the general formula (A)$_3$P, wherein A is hydroxyalkyl.

5. The process of claim 4 wherein the first functional group and the second functional group of the linking agent have the formula —CONHNH$_2$.

6. The process of claim 5 wherein the crosslinking agent is tris(hydroxymethyl)phosphine.

7. The process of claim 6 wherein the linking agent is adipic dihydrazide.

8. The process of claim 1 wherein the substrate comprises a polymeric material selected from polyolefins, polyacrylics, polyvinyl chloride, polyamides, polyurethanes, polyurethaneureas, silicone urethane copolymers, polyvinylpyrrolidone, polyvinyl alcohols, cellulosic materials, polystyrene, polyesters, fluorinated polymers, silicone polymers, natural rubber, polycarbonates, and mixtures thereof.

9. The process of claim 1 wherein the antithrombogenic agent is selected from heparin, prostaglandins, urokinase, streptokinase, sulfated polysaccharide, albumin and mixtures thereof.

10. The process of claim 9 wherein the antithrombogenic agent is heparin.

11. The process of claim 9 wherein:

the polymer is a polyamide, and step (a) comprises: (i) reacting a monomer selected from unsaturated carboxylic acids, esters of unsaturated carboxylic acids, anhydrides of unsaturated carboxylic acids, and mixtures thereof, and a first amine to form an intermediate reaction product, wherein the first amine is selected from RR$_1$NH, RNH$_2$, RR$_1$NH$_2^+$, RNH$_3^+$ and mixtures thereof, wherein R and R$_1$ can be the same or different and each contain between about 1 and 50 carbon atoms and are optionally substituted with heteroatoms oxygen, nitrogen, sulfur, and phosphorus and combinations thereof; and (ii) reacting the intermediate reaction product and a second amine to form the polyamide, wherein the second amine is selected from R$_2$R$_3$NH, R$_2$NH$_2$, R$_2$R$_3$NH$_2^+$, R$_2$NH$_3^+$ and mixtures thereof, wherein R$_2$ and R$_3$ can be the same or different and each contain between about 1 and 50 carbon atoms and are optionally substituted with heteroatoms oxygen, nitrogen, sulfur, and phosphorus and combinations thereof, wherein multiple of the R, R$_1$, R$_2$, and R$_3$ are in vertically aligned spaced relationship along a backbone formed by the polyamide.

12. The process of claim 11 wherein R and R$_1$ are alkyl.

13. The process of claim 12 wherein the first amine is tetradecylamine.

14. The process of claim 11 wherein the second amine is a polyalkylene polyamine.

15. The process of claim 14 wherein the polyalkylene polyamine is pentaethylenehexamine.

16. The process of claim 11 wherein the monomer is selected from unsaturated dicarboxylic acids, esters of unsaturated dicarboxylic acids, anhydrides of unsaturated dicarboxylic acids, and mixtures thereof.

17. The process of claim 16 wherein the monomer is selected from maleic anhydride, maleic acid esters, and mixtures thereof.

18. The process of claim 9 wherein:

the polymer is a polyamide, and step (a) comprises: (i) reacting an α,β-unsaturated lactone and a first amine to form an intermediate reaction product, wherein the first amine is selected from RR$_1$NH, RNH$_2$, RR$_1$NH$_2^+$, RNH$_3^+$ and mixtures thereof, wherein R and R$_1$ can be the same or different and each contain between about 1 and 50 carbon atoms and are optionally substituted with heteroatoms oxygen, nitrogen, sulfur, and phosphorus and combinations thereof; and (ii) reacting the intermediate reaction product and a second amine to form the polyamide, wherein the second amine is selected from R$_2$R$_3$NH, R$_2$NH$_2$, R$_2$R$_3$NH$_2^+$, R$_2$NH$_3^+$ and mixtures thereof, wherein R$_2$ and R$_3$ can be the same or different and each contain between about 1 and 50 carbon atoms and are optionally substituted with heteroatoms oxygen, nitrogen, sulfur, and phosphorus and combinations thereof, wherein multiple of the R, R$_1$, R$_2$, and R$_3$ are in vertically aligned spaced relationship along a backbone formed by the polyamide.

19. The process of claim 18 wherein R and R$_1$ are alkyl.

20. The process of claim 19 wherein the first amine is tetradecylamine.

21. The process of claim 18 wherein the second amine is a polyalkylene polyamine.

22. The process of claim 21 wherein the polyalkylene polyamine is pentaethylenehexamine.

23. The process of claim 18 wherein the lactone is 2(5H)-furanone.

24. A process for rendering the surface of a substrate non-thrombogenic, the process comprising:

(a) reacting a monomer selected from unsaturated carboxylic acids, esters of unsaturated carboxylic acids, anhydrides of unsaturated carboxylic acids, and mixtures thereof, and a first amine to form an intermediate reaction product, wherein the first amine is selected from RR$_1$NH, RNH$_2$, RR$_1$NH$_2^+$, RNH$_3^+$ and mixtures thereof, wherein R and R$_1$ can be the same or different and each contain between about 1 and 50 carbon atoms and are optionally substituted with heteroatoms oxygen, nitrogen, sulfur, and phosphorus and combinations thereof;

(b) reacting the intermediate reaction product and a second amine to form a polyamide, wherein the second amine is selected from R$_2$R$_3$NH, R$_2$NH$_2$, R$_2$R$_3$NH$_2^+$, R$_2$NH$_3^+$ and mixtures thereof, wherein R$_2$ and R$_3$ can be the same or different and each contain between about 1 and 50 carbon atoms and are optionally substituted with heteroatoms oxygen, nitrogen, sulfur, and phosphorus and combinations thereof, wherein multiple of the R, R$_1$, R$_2$, and R$_3$ are in vertically aligned spaced relationship along a backbone formed by the polyamide and at least two side chains of the polyamide contain an amino group;

(c) mixing the polyamide with a crosslinking agent selected from the group consisting of phosphines having the general formula (A)$_3$P, wherein A is hydroxyalkyl, and with a linking agent having two functional groups of the formula —CONHNH$_2$ to produce a polymer solution;

(d) providing a substrate;

(e) coating at least a portion of the substrate with the polymer solution to produce a crosslinked polymer coating on the substrate; and (f) contacting at least a portion of the crosslinked polymer coating on the substrate with heparin whereby the heparin covalently bonds to the second functional group of the linking agent.

25. The process of claim 24 wherein R and $R_1$ are alkyl and the second amine is a polyalkylene polyamine.

26. The process of claim 25 wherein the monomer is selected from maleic anhydride, maleic acid esters, and mixtures thereof.

27. The process of claim 26 wherein the crosslinking agent is tris(hydroxymethyl)phosphine and the linking agent is adipic dihydrazide.

28. The process of claim 27 wherein the substrate comprises a polymeric material selected from polyolefins, polyacrylics, polyvinyl chloride, polyamides, polyurethanes, polyurethaneureas, silicone urethane copolymers, polyvinylpyrrolidone, polyvinyl alcohols, cellulosic materials, polystyrene, polyesters, fluorinated polymers, silicone polymers, natural rubber, polycarbonates, and mixtures thereof.

29. A process for rendering the surface of a substrate non-thrombogenic, the process comprising:

(a) reacting an α,β-unsaturated lactone and a first amine to form an intermediate reaction product, wherein the first amine is selected from $RR_1NH$, $RNH_2$, $RR_1NH_2^+$, $RNH_3^+$ and mixtures thereof, wherein R and $R_1$ can be the same or different and each contain between about 1 and 50 carbon atoms and are optionally substituted with heteroatoms oxygen, nitrogen, sulfur, and phosphorus and combinations thereof;

(b) reacting the intermediate reaction product and a second amine to form a polyamide, wherein the second amine is selected from $R_2R_3NH$, $R_2NH_2$, $R_2R_3NH_2^+$, $R_2NH_3^+$ and mixtures thereof, wherein $R_2$ and $R_3$ can be the same or different and each contain between about 1 and 50 carbon atoms and are optionally substituted with heteroatoms oxygen, nitrogen, sulfur, and phosphorus and combinations thereof, wherein multiple of the R, $R_1$, $R_2$, and $R_3$ are in vertically aligned spaced relationship along a backbone formed by the polyamide and at least two side chains of the polyamide contain an amino group;

(c) mixing the polyamide with a crosslinking agent selected from the group consisting of phosphines having the general formula $(A)_3P$, wherein A is hydroxyalkyl, and with a linking agent having two functional groups of the formula —$CONHNH_2$ to produce a polymer solution;

(d) providing a substrate;

(e) coating at least a portion of the substrate with the polymer solution to produce a crosslinked polymer coating on the substrate; and (f) contacting at least a portion of the crosslinked polymer coating on the substrate with heparin whereby the heparin covalently bonds to the second functional group of the linking agent.

30. The process of claim 29 wherein R and $R_1$ are alkyl and the second amine is a polyalkylene polyamine.

31. The process of claim 30 wherein the lactone is 2(5H)-furanone.

32. The process of claim 31 wherein the crosslinking agent is tris(hydroxymethyl)phosphine and the linking agent is adipic dihydrazide.

33. The process of claim 32 wherein the substrate comprises a polymeric material selected from polyolefins, polyacrylics, polyvinyl chloride, polyamides, polyurethanes, polyurethaneureas, silicone urethane copolymers, polyvinylpyrrolidone, polyvinyl alcohols, cellulosic materials, polystyrene, polyesters, fluorinated polymers, silicone polymers, natural rubber, polycarbonates, and mixtures thereof.

34. An article having a non-thrombogenic surface, the article comprising:

a substrate;

a coating disposed on at least a portion of the substrate, the coating comprising a crosslinked chemical combination of (i) a polymer having side chains along a backbone forming the polymer, at least two of the side chains containing an amino group, (ii) a crosslinking agent containing at least two functional groups that react with the amino groups, and (iii) a linking agent containing a first functional group and a second functional group, the first functional group reacting with a third functional group of the crosslinking agent; and an antithrombogenic agent covalently bonded to the second functional group of the linking agent.

35. The article of claim 34 wherein:

the polymer is a polyamide, and the polymer is synthesized by (i) reacting a monomer selected from unsaturated carboxylic acids, esters of unsaturated carboxylic acids, anhydrides of unsaturated carboxylic acids, and mixtures thereof, and a first amine to form an intermediate reaction product, wherein the first amine is selected from $RR_1NH$, $RNH_2$, $RR_1NH_2^+$, $RNH_3^+$ and mixtures thereof, wherein R and $R_1$ can be the same or different and each contain between about 1 and 50 carbon atoms and are optionally substituted with heteroatoms oxygen, nitrogen, sulfur, and phosphorus and combinations thereof, and (ii) reacting the intermediate reaction product and a second amine to form the polyamide, wherein the second amine is selected from $R_2R_3NH$, $R_2NH_2$, $R_2R_3NH_2^+$, $R_2NH_3^+$ and mixtures thereof, wherein $R_2$ and $R_3$ can be the same or different and each contain between about 1 and 50 carbon atoms and are optionally substituted with heteroatoms oxygen, nitrogen, sulfur, and phosphorus and combinations thereof, wherein multiple of the R, $R_1$, $R_2$, and $R_3$ are in vertically aligned spaced relationship along a backbone formed by the polyamide.

36. The article of claim 35 wherein R and $R_1$ are alkyl.

37. The article of claim 36 wherein the first amine is tetradecylamine.

38. The article of claim 35 wherein the second amine is a polyalkylene polyamine.

39. The article of claim 38 wherein the polyalkylene polyamine is pentaethylenehexamine.

40. The article of claim 35 wherein the monomer is selected from unsaturated dicarboxylic acids, esters of unsaturated dicarboxylic acids, anhydrides of unsaturated dicarboxylic acids, and mixtures thereof.

41. The article of claim 34 wherein the monomer is selected from maleic anhydride, maleic acid esters, and mixtures thereof.

42. The article of claim 34 wherein:

the polymer is a polyamide, and the polymer is synthesized by (i) reacting an α,β-unsaturated lactone and a first amine to form an intermediate reaction product, wherein the first amine is selected from $RR_1NH$, $RNH_2$, $RR_1NH_2^+$, $RNH_3^+$ and mixtures thereof, wherein R and $R_1$ can be the same or different and each contain between about 1 and 50 carbon atoms and are optionally substituted with heteroatoms oxygen, nitrogen, sulfur, and phosphorus and combinations thereof, and (ii) reacting the intermediate reaction product and a second amine to form the polyamide, wherein the second amine is selected from $R_2R_3NH$, $R_2NH_2$, $R_2R_3NH_2^+$, $R_2NH_3^+$ and mixtures thereof, wherein $R_2$ and $R_3$ can be the same or different and each contain between about 1 and 50 carbon atoms and are optionally substituted with heteroatoms oxygen, nitrogen, sulfur, and phosphorus and combinations thereof, wherein multiple of the R, $R_1$, $R_2$, and $R_3$ are in vertically aligned spaced relationship along a backbone formed by the polyamide.

43. The article of claim 42 wherein R and $R_1$ are alkyl.

44. The article of claim 43 wherein the first amine is tetradecylamine.

45. The article of claim 42 wherein the second amine is a polyalkylene polyamine.

46. The article of claim 45 wherein the polyalkylene polyamine is pentaethylenehexamine.

47. The article of claim 42 wherein the lactone is 2(5H)-furanone.

48. The article of claim 34 wherein the antithrombogenic agent is selected from heparin, prostaglandins, urokinase, streptokinase, sulfated polysaccharide, albumin and mixtures thereof.

49. The article of claim 48 wherein the antithrombogenic agent is heparin.

50. The article of claim 49 wherein heparin is present on the surface of the article at a concentration of about 5 to about 10 micrograms per square centimeter.

51. The article of claim 34 wherein the substrate comprises a polymeric material selected from polyolefins, polyacrylics, polyvinyl chloride, polyamides, polyurethanes, polyurethaneureas, silicone urethane copolymers, polyvinylpyrrolidone, polyvinyl alcohols, cellulosic materials, polystyrene, polyesters, fluorinated polymers, silicone polymers, natural rubber, polycarbonates, and mixtures thereof.

52. The article of claim 34 wherein the crosslinking agent is selected from the group consisting of phosphines having the general formula $(A)_3P$, wherein A is hydroxyalkyl.

53. The article of claim 52 wherein the crosslinking agent is tris(hydroxymethyl)phosphine.

54. The article of claim 34 wherein the linking agent is a polyhydrazide.

55. The article of claim 54 wherein the linking agent is adipic dihydrazide.

* * * * *

UNITED STATES PATENT AND TRADEMARK OFFICE
CERTIFICATE OF CORRECTION

PATENT NO. : 6,509,104 B2 Page 1 of 1
DATED : January 21, 2003
INVENTOR(S) : Huang, McDonald, Wright and Taylor It is certified that error appears in the above-identified patent and that said Letters Patent is hereby corrected as shown below:

<u>Column 1,</u>
Line 4, insert:

-- STATEMENT REGARDING FEDERALLY SPONSORED RESEARCH OR DEVELOPMENT

This Invention was made with Government support under NREL Subcontract NO. XXE-9-29058-01, Prime Contract No. DE-AC36-98GO10337 awarded by the Department of Energy. The Government has certain rights in this invention. --

Signed and Sealed this

Twenty-ninth Day of July, 2003

JAMES E. ROGAN
*Director of the United States Patent and Trademark Office*